(12) United States Patent
Witztum et al.

(10) Patent No.: US 7,575,873 B2
(45) Date of Patent: Aug. 18, 2009

(54) REAGENTS FOR DIAGNOSING, IMAGING AND TREATING ATHEROSCLEROTIC DISEASE

(75) Inventors: Joseph L. Witztum, Sand Diego, CA (US); Sotirios Tsimikas, San Diego, CA (US); Wulf Palinski, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 119 days.

(21) Appl. No.: 10/706,659

(22) Filed: Nov. 12, 2003

(65) Prior Publication Data

US 2004/0120893 A1    Jun. 24, 2004

Related U.S. Application Data

(62) Division of application No. 09/699,131, filed on Oct. 26, 2000, now Pat. No. 6,716,410.

(60) Provisional application No. 60/161,493, filed on Oct. 26, 1999.

(51) Int. Cl.
*G01N 33/563* (2006.01)
*G01N 33/53* (2006.01)
*A61K 39/395* (2006.01)

(52) U.S. Cl. .................. 435/7.1; 436/512; 436/547; 435/7.21; 435/70.21; 424/130.1; 530/300; 530/350; 530/387.1

(58) Field of Classification Search ................. 436/512, 436/547; 435/7.1, 70.21; 424/130.1; 530/387.1
See application file for complete search history.

(56) References Cited

U.S. PATENT DOCUMENTS

| 5,330,910 | A | 7/1994 | Young et al. |
| 5,460,947 | A | 10/1995 | Young et al. |
| 6,225,070 | B1 * | 5/2001 | Witztum et al. .............. 435/7.1 |
| 6,375,925 | B1 | 4/2002 | Witztum et al. |

FOREIGN PATENT DOCUMENTS

| WO | WO 94/23302 | 10/1994 |
| WO | WO/98/21581 | 5/1998 |

OTHER PUBLICATIONS

Sotiriadou et al., DELTA-IK17: An antigen expressed on human lymphocytes. International Journal of BiologicalMarkers, 1996, vol. 11, No. 4, pp. 183-189.*
Jein et al., J Med Chem., 1994, 37, 2100-2105.*
Kuduk et al. Bio & Med Chemistry Letters, 10, 2000, 1303-1306.*
Peipp and Valerius, Biochemistry Society Transactions, 2002, vol. 30, part 4, pp. 507-511.*
Waldmann, Science, vol. 252, Jun. 21, 1991, pp. 1657-1662.*
Hoorko S. Miller, E. Dudl E. et al Antiphospholipid antibodies are directed against epitopes of oxidized phospholipids:recognition of cardiolipin by monoclonal antibodies to epitopes of oxidized LDL. J. Clin. Invest.;1996:98; 815-825.
Huse WD, Sastry L, Iverson SA, Klang AS, Alting-Mees M. Burton DR, Benkovic SJ, Lerner RA. Generation of a large combinatorial library of immunoglobulin repertoire in phage lambda. Science. 1989;246:1275-1281.
Palinski W. Horkko, S. Miller et al. Cloning of monoclonal autoantibodies to epitopes of oxidized lipoproteins for apo E-deficient mice. Demostration of epitopes of oxidezed LDL in human plasma. J.Clon.Invest 1996;98:800-814.
Shaw P.X, Horkko, S. Chang, M-K Curtiss, L.K. Palinski, W. Silverman, G.J. and Witztum, J.L. Natural antibodies with T15 Idiotype may act in atheosclerosis, apoptotoc clearance and protective immunity. J. Clin, Invest. 105:1731-40, 2000.
Wu CC, Chang SW, Chen MS, Lee YT. Early change of vascular permeability in hypercholoesterloemic rabbits. Arterioscler Thomb Vasc Biol. 1995, 15-529-533.
Libby P. et al. Stabilizing of atherosclerotic plaques: New mechanisms and clinical targets. Nature Medicine. vol. 8, No. 11, 1257-1262-Nov. 2002.
Narula, J. et al. Strategic targeting of atherosclerotic lesions. Journal of Nucelar Cardiology, Part 1, pp. 81-90 Jan./Feb. 1999.
Strauss, H.W. Imaging of atheosclerosis—A worthy challenge. Journal of Nucelar Cardiology, vol. 3, No. 3, pp. 278-280 May/Jun. 1996.
Tsimikas, S. et al. In vivo uptake of Radiolabeled MDA2, an oxidation-specific monoclonal antibody provides an accurate measure.. Arterioscler Thromb, Vasc. Biol., vol. 20:689-697.2006.
Holovet, P. et al, Monodialdehyde-modified low density lipoproteins in patients with atherosclerotic disease. J. Clin Invest. vol. 95:2611-9. 1995.
Tsimikas S. Palinski W, Halpern SE, Yeung DW, Curtiss LK, Witztum JL. Radiolabeled MDA2, an oxidation-specific Mab, identifies native atherosclerotic lesions in vivo. J. Nucl. Cardiol. 1999; 6:41-53.
Barbas, CF, et al., "Combinatorial Immunoglobulin Libraries on the Surface of Phage (pphabs): Rapid Selection of Antigen-Specific Fates," METHODS: A Companion to Methods in Enzymology, 1991, 2(2): 119-124, Academic Press, Inc., Burlington, MA.
Chang, M-K, et al., "Monoclonal Antibodies Against Oxidized LDL Bind to Apoptotic Cells and Inhibit Their Phagocytosis by Elicited Macrophages: Evidence That Oxidation Specific Epitopes Mediate Macrophage Recognition," Proc. Nat. Acad. Sci. U.S.A., 1999, 96:6353-.
van der Kooij, MA, et al., "Human Monocyte—Derived Macrophages Express and Approximately 120-kD Ox-LDL Binding Protein With Strong Identity to CD 68", 1997, 17(11): 3107-3116.

* cited by examiner

*Primary Examiner*—Lisa V Cook
(74) *Attorney, Agent, or Firm*—Joseph R. Baker, Jr.; Gavrilovich Dodd & Lindsey LLP

(57) ABSTRACT

The invention provides a novel human Mab Fab, cloned by phage display, and its use in diagnostic and therapeutic methods. In particular the invention provides a method for analyzing the OxLDL components of atherosclerotic plaques in vivo and a means to determine their relative pathology. As the method is based on a human Fab rather than a mouse Mab, the progress or regression of the disease may be monitored over time. The antibody may also be used for the analysis of surgical or serum samples ex vivo for the presence of OxLDL. The antibody may also be used to target therapeutic agents to the site of atherosclerotic plaques or may have use as a therapeutic agent itself.

8 Claims, No Drawings

SEQUENCE LISTING

<160> NUMBER OF SEQ ID NOS: 2

<210> SEQ ID NO 1
<211> LENGTH: 603
<212> TYPE: DNA
<213> ORGANISM: Homo sapiens
<220> FEATURE:
<221> NAME/KEY: CDS

<400> SEQUENCE: 1

```
atg gcc gag gtg cag ctg ctc gag tcg ggg gga gac ttg gta cag         45
Met Ala Glu Val Gln Leu Leu Glu Ser Gly Gly Asp Leu Val Gln
1               5                   10                  15 cct ggg ggg tcc ctg aga ctc tcc tgt ata gtc tct gga tcc acc         90
Pro Gly Gly Ser Leu Arg Leu Ser Cys Ile Val Ser Gly Ser Thr
                20                  25                  30 ttc agc aac tat gcc atg agt tgg gtc cgc cag gct cca ggg aag        135
Phe Ser Asn Tyr Ala Met Ser Trp Val Arg Gln Ala Pro Gly Lys
                35                  40                  45 gga ctg gag tgg gtc tca gcg att agt ggt act ggt cgt agc aca        180
Gly Leu Glu Trp Val Ser Ala Ile Ser Gly Thr Gly Arg Ser Thr
                50                  55                  60 aac tac gca gac tcc gtg aag ggc cgg ttc acc atc tcc aga gac        225
Asn Tyr Ala Asp Ser Val Lys Gly Arg Phe Thr Ile Ser Arg Asp
                65                  70                  75 aat tcc aag gac acg ctg tat ctg gaa atg aac agc ctg aga gcc        270
Asn Ser Lys Asp Thr Leu Tyr Leu Glu Met Asn Ser Leu Arg Ala
                80                  85                  90 gag gac acg gcc aca tat tat tgt acg aga acc ccc cgg atc gat        315
Glu Asp Thr Ala Thr Tyr Tyr Cys Thr Arg Thr Pro Arg Ile Asp
                95                  100                 105 ttt tgg aac ata gcc aac cgt cac ttt gac tac tgg ggc cag gga        360
Phe Trp Asn Ile Ala Asn Arg His Phe Asp Tyr Trp Gly Gln Gly
                110                 115                 120 acc cgg gtc acc gtc tcc tca gcc tcc acc aag ggc cca tcg gtc        405
Thr Arg Val Thr Val Ser Ser Ala Ser Thr Lys Gly Pro Ser Val
                125                 130                 135 ttc ccc ctg gca ccc tcc tcc aag agc acc tct ggg ggc aca gcg        450
Phe Pro Leu Ala Pro Ser Ser Lys Ser Thr Ser Gly Gly Thr Ala
                140                 145                 150 gcc ctg ggc tgc ctg gtc agg gac tac ttc ccc gaa ccg gtg acg        495
Ala Leu Gly Cys Leu Val Arg Asp Tyr Phe Pro Glu Pro Val Thr
                155                 160                 165 gtg tcg tgg aac tca ggc gcc ctg acc agc ggc gtg cac acc ttc        540
Val Ser Trp Asn Ser Gly Ala Leu Thr Ser Gly Val His Thr Phe
                170                 175                 180 ccg gct gtc cta cag tcc tca gga ctc tac tcc ctc agc agc gtg        585
Pro Ala Val Leu Gln Ser Ser Gly Leu Tyr Ser Leu Ser Ser Val
                185                 190                 195
```

```
                                                            -continued gtg acc gtg ccc tcc agc                                         603
Val Thr Val Pro Ser Ser
                200

<210> SEQ ID NO 2
<211> LENGTH: 456
<212> TYPE: DNA
<213> ORGANISM: Homo sapiens
<220> FEATURE:
<221> NAME/KEY: CDS

<400> SEQUENCE: 2 gtg ttg aca cag tca cca gcc acc ctg tct ttg tct cca ggg gaa       45
Val Leu Thr Gln Ser Pro Ala Thr Leu Ser Leu Ser Pro Gly Glu
 1               5                  10                  15 aga gtc acc ctc tcc tgc agg gcc agt cag agt gtt agc agc tcc       90
Arg Val Thr Leu Ser Cys Arg Ala Ser Gln Ser Val Ser Ser Ser
                20                  25                  30 tta gcc tgg tac caa cag aaa cct ggc cag gct ccc agg ctc ctc      135
Leu Ala Trp Tyr Gln Gln Lys Pro Gly Gln Ala Pro Arg Leu Leu
            35                  40                  45 atc tat gat gca tcc aac agg gcc act ggc gtc cca gcc agg ttc      180
Ile Tyr Asp Ala Ser Asn Arg Ala Thr Gly Val Pro Ala Arg Phe
        50                  55                  60 agt ggc agt ggg tct ggg aca gac ttc act ctc acc atc agc ggc      225
Ser Gly Ser Gly Ser Gly Thr Asp Phe Thr Leu Thr Ile Ser Gly
    65                  70                  75 cta gag cct gaa gat ttt gca gtt tat tac tgt cag cag cgt tac      270
Leu Glu Pro Glu Asp Phe Ala Val Tyr Tyr Cys Gln Gln Arg Tyr
80                  85                  90 aac tgg cct ccg aag tac act ttt ggc cag ggg acc aag ctg gag      315
Asn Trp Pro Pro Lys Tyr Thr Phe Gly Gln Gly Thr Lys Leu Glu
                95                 100                 105 atc aga cga act gtg gct gca cca tct gtc ttc atc ttc ccg cca      360
Ile Arg Arg Thr Val Ala Ala Pro Ser Val Phe Ile Phe Pro Pro
            110                 115                 120 tct gat gag cag ttg aaa tct gga act gcc tct gtt gtg tgc ctg      405
Ser Asp Glu Gln Leu Lys Ser Gly Thr Ala Ser Val Val Cys Leu
        125                 130                 135 ctg aat aac ttc tat ccc aga gag gcc aaa gta cag tgg aag gtg      450
Leu Asn Asn Phe Tyr Pro Arg Glu Ala Lys Val Gln Trp Lys Val
    140                 145                 150 gga taa                                                          456
Gly
```

REAGENTS FOR DIAGNOSING, IMAGING AND TREATING ATHEROSCLEROTIC DISEASE

CROSS-REFERENCES TO RELATED APPLICATIONS

This application is a divisional application and claims priority to U.S. patent application Ser. No. 09/699,131, filed Oct. 26, 2000 (Now U.S. Pat. No. 6,716,410), which application claims the benefit of priority of U.S. Provisional Application Ser. No. 60/161,493 filed Oct. 26, 1999 which is incorporated herein by reference in its entirety.

GOVERNMENT SUPPORT

The invention was made with government support under grant numbers HL-56989, HL-57505 and HL-07444, all awarded by the National Institutes of Health. The government may have certain rights in the invention.

SEQUENCE LISTING

A sequence listing filed in accordance with 37 C.F.R. § 1.82appended hereto is hereby incorporated by reference.

BACKGROUND OF THE INVENTION

1. Field of the Invention

The invention herein relates to a novel human monoclonal antibody fragment (Fab), cloned by phage display that binds specifically to oxidized forms of low density lipoproteins (OxLDL) and not native LDL. More particularly, it relates to the use of the antibody for improved methods of diagnosis and treatment of atherosclerosis.

2. Description of Prior Art

Atherosclerosis is a chronic inflammatory disease that results from hyperlipidemia and a complex interplay of a variety of environmental, metabolic and genetic risk factors. The oxidation of low density lipoprotein (LDL) plays a central, if not obligatory role, in the atherogenic process. Early studies showed that acetylation of LDL greatly enhanced its uptake by macrophges and that the uptake occurred via "scavenger receptors" which were distinct from the classical LDL receptor. Unlike most receptors, these scavenger receptors were not downregualted following uptake of OxLDL. Due to the excessive uptake of OxLDL and its associated lipid by the macrophages, the cells obtained a characteristic foam-like appearance. The appearance of such cells is one of the first hallmarks of atherosclerotic disease. Foam cells accumulate within the intima (under the endothelial lining) of the vessel walls where they become unstable and plaques, the hallmarks of more advanced disease. Inflammatory conditions develop leading to the development of complicated lesions.

There is much evidence that OxLDL contributes to atherogenesis by a number of mechanisms. The oxidation of polyunsaturated fatty acids in phospholipids of lipoproteins generates many breakdown products such as malondialdehyde (MDA), 4-hydroxynonenal (4-HNE), and other reactive moieties attached to oxidized phospholipids. Many of these intermediate products are highly reactive and can interact with lysine residues of associated proteins and phospholipids to generate various adducts. These adducts are known to occur in vivo and are immunogenic. In murine models of atherosclerosis, such as apo-E deficient mice (ApoE$^{-/-}$) mice, atherosclerosis is correlated with the development of high titers of autoanitbodies to varous oxidation specfic epitopes of OxLDL. The consequences of such cellular and humoral responses are still poorly understood, but under certain conditions they can clearly modify the natural history of the disease.

It is generally accepted that it is the composition of atherosclerotic lesions, in particular the content of lipids, OxLDL, foam cells, and smooth muscle cells, that determines their properties. Foam cells are often found in the sites of lesion that are susceptible to rupture. Activated macrophages recruited to clear the apoptotic and necrotic foam cells, as well as OxLDL, secrete factors that weaken the plaque. Human pathology studies have shown that atheromas containing a large necrotic core, thin fibrous cap and large numbers of macrophage/foam cells in the shoulder are more predisposed to plaque rupture and thrombosis. These lesions, which frequently appear as mild or moderate coronary stenoses in angiographic studies, are characterized pathologically as large atheroma with extensive lipid pools exceeding 40% of plaque areas. Angiography only provides a measure of arteial lumen, but fails to detect vessel wall pathology. Diagnostic methods that provide a measure of the overall extent of the atherosclerotic lesion, with an emphasis on OxLDL and lipid content, would therefore be desirable. Moreover, the lipid core of atheromas can be assumed to contain extensive oxidized lipids that accumulated within foam cells and set free when cells undergo necrosis and apoptosis.

Non-invasive detection of atherosclerotic lesions is currently not clinically feasable. The gold standard for diagnosing atherosclerosis is angiography which detects abnormal vessel lumen contours caused by encroaching atherosclerosis but does not directly identify abnormalities of the vessel wall. The widely recognized limitations of angiography include poor correlation with functional stenosis, interobserver and intraobserver variability, underestimation of the extent of disease because of diffusely atherosclerotic vessels, and arterial remodeling. B mode and ultravascular ultrasonography can detect intima/media thickening and calcification of vascular walls, but cannot clearly assess specific tissue characteristics. Electron beam computed tomography detects only calcium in vessel walls. Magnetic resonance imaging is still an investigational tool for the detection of plaque components.

Human studies have suggested that plaque rupture frequently occurs in nonangiographically significant lesions that contain abundant lipid-laden macrophages and large lipid pools within atheromas. Therefore imaging of atherosclerosis directed at lipid rich areas would be of value, not only in detecting the extent of lesion burden, but also in the detecting clinically silent but "active" lesions. Previous radioscintographic imaging agents have been limited by poor specificity, low in vivo uptake in atherosclerotic plaque, and slow elimination from the circulation, resulting in poor lesion/background ratios. Various imaging agents have been used including radiolabeled LDL, fragments of apolipoprotein B, autologous platelet and antiplatelet antibodies, non-specific antibodies and Fc fragments, hematoporphyrin derivatives, and anti-malonic acid monoclonal antibodies (Mabs).

OxLDL specific antibodies have been isolated from human and rabbit atherosclerotic lesions which contain tightly bound IgGs that recognize epitopes of OxLDL in vitro and stains atherosclerotic lesions in vitro. Mouse hybridoma cell lines have been generated for the production of Mabs against OxLDL and the antibodies were found to bind specifically to oxidized, rather than native phospholipids. However all of the antibodies previously described were monospecific, binding to only one form of OxLDL. The EO series of mouse Mabs described by Palinski et al. (1996), were able to bind either OxLDL or MDA-LDL, not both. Similarly, MDA2 and NA59, mouse Mabs described in other studies, bind MDA-LDL and HNE-LDL respectively. Most importantly, these mouse antibodies are limited in their usefulness for human applications in vivo as they illicit an immune response that prohibits their repeated administration.

Hybridoma technology, which is widely used in generating murine Mabs, is less successful in producing human hybridomas. Epstein Barr Virus (EBV) may be used to immortalize human lymphocytes, however due to the wide variety of neoepitopes in OxLDL, acquisition of human Mabs to many different epitopes would be arduous. Furthermore, clones derived by this technique are frequently unstable and low secretors. Additionally, the EBV-transformants produce IgM antibodies, while anti-OxLDL antibodies can be both IgG and IgM isotypes.

Phage display combinatorial library technology provides a useful method to generate human Mabs (Barbas and Lerner, 1991; Huse, et al., 1989). The libraries made from lymphocyte mRNA may consist of up to $10^8$ recombinants of monoclonal Fab repertoires. By displaying the library on a filamentous phage surface and panning against a model epitope, monoclonal Fab antibodies can be selected and analyzed for their immunological properties and biological activities. Fabs are ideal for use in both therapeutic and diagnostic methods as they can be produced in large quantities inexpensively and they are innately non-immunogenic. Additionally, they are not whole antibody molecules which can initiate a cascade of immune responses upon binding to their antigen.

SUMMARY OF THE INVENTION

The invention herein is the discovery of an antibody that binds to a novel epitope of OxLDL and MDA-LDL, but not native LDL, and its uses in imaging of atherosclerotic plaques, as a means for targeting therapeutics, and as a therapeutic itself or model structure for the development of novel therapeutics for the treatment of atherosclerosis.

The invention is the discovery of a cloned human monoclonal Fab isolated from a phage display library generated from mRNA from peripheral blood mononuclear cells (PBMC) from a patient who was found to have high antibody titers to MDA-LDL. After serial rounds of panning, a monoclonal IgG Fab antibody was isolated which bound specifically to both MDA-LDL and copper-induced OxLDL, but did not bind native LDL, as determined by both direct and competition binding assays. The Fab was found to bind specifically to atherosclerotic plaques, both in vivo and in vitro in human, mouse, and rabbit tissue. Furthermore, it was found to inhibit the uptake of OxLDL by macrophages, suggesting that the epitope on OxLDL defined by the Fab may be an important ligand for the macrophage scavenger receptors in normal clearance or atherogenesis. We have named the Fab IK17.

Additionally, the invention overcomes the deficiencies of prior art detection methods for atherosclerotic lesions by the use of IK17. The invention describes a new method to non-invasively image the atherosclerotic lesions themselves by the use of the use of a Fab conjugated to an appropriate molecule for detection. This further provides a means for particular discrimination of lipid rich components and oxidation rich components in vivo. The non-invasive nature of the imaging method using the invention reduces cost and risks to the patient allowing the method to be used as a means to monitor the effects of a treatment regimen, as well as a primary detection method. Detection methods for use with the instant invention include, but are not limited to, magnetic resonance imaging (MRI). computer axial tomography (CAT) scan, positron emission tomography (PET) scan, electron beam, computed tomography (CT) scan, single photon emission computed tomography (SPECT) imaging, gamma imaging, angiography, intravascular ultrasound. and intravascular radioactive and fluorescent detection. The imaging method disclosed herein is more sensitive than previous methods allowing for the detection of atherosclerosis, both coronary and non-coronary, before the occurrence of significant stenosis, allowing for earlier intervention. It also provides a means for observing the vessel itself and assaying the amount of lipid present in the lesion, providing a prognostic indicator and a method to grade the pathology of the lesion. It is a method to quantitatively monitor the effects of a treatment regimen as human antibodies will not induce an immune response. This type of surveillance cannot be performed with murine antibodies due to the potentially life threatening immune response to repeated administration of non-human antibodies.

The invention allows for the improvement of current therapeutics and the development of novel ones for the treatment of atherosclerosis. The Fab provides a means for targeting therapeutic agents to the site of the plaques by covalently linking a thrombolytic agent, antioxidant, antimetalloproteinase or other therapeutic agent to the antibody. Alternatively, IK17 itself, or small molecule analogs of IK17, could be used as drugs. IK17 is known to inhibit the uptake of OxLDL by macrophages, thus inhibiting the formation of foam cells. Inhibition of foam cell formation could decrease the deposition of lipids on the vessel wall and slow the progression of the disease.

DETAILED DESCRIPTION OF THE INVENTION

The invention herein is the discovery of a human monoclonal Fab that we have named IK 17 that binds specifically to both OxLDL and MDA-LDL, but not native LDL, and uses of the Fab in the improved detection and treatment of atherosclerosis. This is the first discovery of an antibody that recognizes two forms of modified LDL. IK17 was isolated from a phage display library prepared from RNA from PMNCs from a donor with coronary heart disease. It was found to be specific to Cu-OxLDL and MDA-LDL by a number of direct and competition binding assays using purified LDL. It was also found to be highly effective in a macrophage uptake assay, inhibiting the phagocytosis of both OxLDL and apoptotic cells. Additionally, the Fab was found to be useful for labeling atherosclerotic plaques, both in vitro and in viva. Radioactively labeled IK17 injected into mice was found to co-localize to atherosclerotic plaques as determined by Sudan™ staining.

IK17 was cloned from a combinatorial Fab library by methods known to those skilled in the art. Briefly, human plasma samples were screened for the presence of antibodies to OxLDL using a chemiluminescence assay (Hörkkö et al., 1996). A patient was identified as having a high antibody titer to MDA-LDL. PBMC were isolated from the patient and total RNA was extracted and used as a template to synthesize cDNA. The cDNA was used as a template for PCR amplification of the light and heavy chains, as described previously (Barbas and Lerner, 1991). Subsequently, 3 pairs of extension primers were used for secondary amplification to add restriction sites to each of the three classes of fragments, V-kappa, V-lambda, and VH.

PCR products of the expected size were cloned into the phage display vector pComb3H. The resultant phagemid DNA was transformed into XL-1 blue *E. coli* cells by electroporation. Clones were panned against MDA-LDL coated onto an ELISA plates. A suspension containing approximately $10^9$-$10^{10}$(100μl) of recombinant phage was applied to each coated well and incubated at 37° C. for 1 hour. After incubation, the wells were washed, once after the first round of panning or 10 times after subsequent rounds to remove unbound phage. Bound phage were eluted and used to infect bacteria for amplification by methods well known to one skilled in the art. After the final round of panning, phagemid DNA was prepared to remove gene III which anchors Fab on the phage surface, by endonuclease digestion and religation. The resultant products were transformed into XL1-blue cells to express soluble Fab by induction with isopropyl beta-D-thiogalactopyranoside (IPTG). Cell lysates were prepared and ELISA assays were performed to analyze Fab production and MDA-LDL binding activity. For subsequent experiments, selected monoclonal Fabs were purified using an IgG (Fab) affinity column by methods known to one skilled in the art.

Plasmid DNA containing the VH and VL genes of the Fab was isolated from cells and sequenced using an automated sequencer. Nucleotide sequences were analyzed using the EMBL/GenBank database. Analysis revealed that the repertoire of Fab of the invention light chain uses a v-kappa 3 family gene (Vg/38κ/L6) with the rearrangement to Jκ2. The repertoire of heavy chain uses a VH3 family gene, 3-23/VH26c/DP47, with the rearrangement to JH4b.

The binding specificity of affinity purified Fab was studied by analyzing binding of the purified protein to MDA-LDL, Cu-OxLDL, and native LDL as well as a panel of unrelated protein and nucleic acid antigens, using both direct binding and competition assays. The binding of the Fab was found to be specific to MDA-LDL and Cu-OxLDL, with a preference for MDA-LDL with an affinity of 37 nM. The Fab did not bind significantly to 4-HNE-LDL, nor did it bind to non-specific MDA modified proteins. The Fab was capable of binding both the lipid and protein fractions of the Cu-OxLDL, but did not bind the native LDL, either whole or fractionated The ability of the Fab to localize to atherosclerotic plaques makes it ideal for use in a method for detection of atherosclerotic lesions. The Fab can be produced easily and inexpensively in large quantities, as opposed to antibodies produced from hybridoma cell lines. Additionally, hybridoma lines may be unstable and decrease antibody expression levels over time. As there are no IgG type molecules in the *E. coli* in which the Fab is produced, purification can be carried out in a single affinity purification step. The antibody can be linked to radioisotopes, paramagnetic labels, echogenic liposomes, or other appropriate agents that can be detected by imaging methods, and injected into the host intravenously. After an appropriate time, imaging can be performed, either whole body for diagnostic purposes or locally at specific sites, such as carotid artery, in a quantitative manner to assess the hosts response to a treatment regimen.

LDL and apoptotic cells accumulate at the site of atherosclerotic lesions and likely contribute to the pathology of the disease. However, they could be exploited as a means for targeting drugs to lesions. Drugs for the treatment of atherosclerosis could be targeted to the appropriate site by linking them to the IK17, which in turn binds to its unique, oxidation specific epitope in the lesion. Such a method could be used to reduce the effective dose of drugs currently being used for atherosclerosis by targeting them to and retaining them at the site of lesions. Additionally it could be used to target therapeutic agents with desired activities that were found to be cleared too rapidly to be effective.

As noted above, it was demonstrated that in animal models of atherosclerosis, immunization with MDA-LDL could ameliorate the progression of the disease. IK17 could be administered as a protein or it could be administered using a gene therapy vector, as a means to ameliorate the progression of atherosclerosis.

As the sequence of IK17(SEQ ID 1 and SEQ ID 2) is cloned it could be easily manipulated for a number of purposes. The coding sequence for linker amino acids, such as lysine or cystiene could be added for modification of IK17 with imaging or therapeutic agents. The pharmacodynamic properties of the antibody could be changes to increase stability, plasma clearance and tissue uptake. The sequences of the antigen recognition region could be mutagenized and subjected to additional rounds of screening with phage display against different model compounds to identify other OxLDL binding antibodies. sequences of the antigen recognition region could be mutagenized and subjected to additional rounds of screening with phage display against different model compounds to identify other OxLDL binding antibodies.

PREFERRED EMBODIMENTS

The preferred embodiments of the invention are described below. All publications mentioned herein are incorporated herein by reference to illustrate known methods and/or materials which may be of use in, but not essential to, the practice of the invention.

Preparation of Combinatorial Fab Library and Cloning of an OxLDL Specific Fab

Plasma from patients was screened for the presence of antibodies to epitopes of OxLDL using a highly sensitive chemiluminescent immunoassay (Hörkkö et al., 1996). Antigens used for screening included Cu-OxLDL and MDA-LDL as model epitopes and native LDL as a negative control. These antigens were prepared as described (Palinski et al, 1996). A patient who had serious coronary artery disease was identified as having a high antibody titer to MDA-LDL.

Peripheral blood mononuclear cells were isolated from the patient and total RNA was isolated using RNA STAT-60 (Tel-Test) per the manufacturer's instructions. cDNA was synthesized with oligo dT primer using the Superscript II cDNA Synthesis Kit (Gibco-BRL). PCR reactions were carried out using the cDNA as template. Seventeen pairs of primers, including 4 pairs for immunoglobulin light chain of V-kappa genes and 5 pairs for V-lambda genes, as well as 5 pairs for variable regions of heavy chain (VH genes), as described previously (Barbas and Lerner, 1991). Additionally, 3 pairs of extension primers were used for secondary amplification to add restriction sites to V-kappa, V-lambda, and VH.

PCR products of the expected size were cloned into the phage display vector pComb3H by two steps: the V-kappa or V-lambda fragments were cloned into the SacI and XbaI sites of the vector first, followed by the cloning of the of the VH product into the XhoI and SpeI sites. The resultant phagemid DNA was transformed into XL-1 blue *E. coli* cells by electroporation. Clones were panned against MDA-LDL coated onto an ELISA plate. A suspension containing approximately $10^9$–$10^{10}$ (100 μl) of recombinant phage was applied to each coated well and incubated at 37° C. for 1 hour. After incubation, the wells were washed, once after the first round of panning or 10 times after subsequent rounds, with boric buffered saline (BBS) with 1% BSA. Bound phage were eluted with acetic acid (pH 2.0) and neutralized with 2M Tris buffer (pH 8.5). The eluent from each panning was used to infect bacteria for amplification by methods well known to one in the art.

After the final round of panning, phagemid DNA was prepared from infected bacteria. The DNA was digested with SpeI and NheI, gel purified, self-ligated, and transformed into XL1-blue cells.

Cultures were grown and Fab expression was induced with isopropyl beta-D-thiogalactopyranoside (IPTG). Cell lysates were prepared and ELISA assays were performed to analyze Fab production and MDA-LDL binding activity. For subsequent experiments, selected monoclonal Fabs were purified against an IgG(Fab) affinity column by methods known to one skilled in the art.

Sequence Analysis of Anti MDA-LDL Clones

Cultures were grown and plasmid DNA was isolated for sequencing using an automated sequencer (ABI Prism®). Nucleotide sequences were analyzed using the EMBL/GenBank database. Analysis revealed that the repertoire of Fab of the invention light chain uses a v-kappa 3 family gene (Vg/38k/L6) with the rearrangement to Jk2. The repertoire of heavy chain uses a VH3 family gene, 3-23/VH26c/DP47, with the rearrangement to JH4b.

Macrophage OxLDL binding Assay

To confirm the capacity of the Fab to inhibit binding of OxLDL to macrophage scavenger receptors, a macrophage binding assay was performed. Mouse peritoneal macrophages were elicited by intraperitoneal injection fo 2 ml of thioglycollate medium (Difco Laboratories) three days prior to harvesting the cells by saline lavage. The macrophages were plate in 24-well clustered dishes at a density of $1 \times 10^6$ cells per well in RPMI 1640 supplemented with 5% fetal calf serum (FCS). Non-adherent cells were removed after three hours and the medium was replaced for overnight incubation.

The binding or degradation of $^{125}$I-Cu-OxLDL to macrophages was determined using methods of Goldstein et al. as previously described (Hörrkö, et al., 1999).

For the binding assay, cells were kept on ice for the entire procedure to prevent the internalization of the OxLDL. Cells were incubated at 4° C. for 30 minutes in serum free media before the addition of $^{125}$I-Cu-OxLDL in the absence or presence of competitors including non-radioactive Cu-OxLDL, a mouse monoclonal directed against OxLDL, the Fab of the invention, and human IgG Fab. After three hours, cells were washed with ice cold PBS with 1% BSA and then solubilized in 0.2 N NaOH. Aliquots were removed for quanitfication of protein and radioactivity.

IK17 was able to inhibit the binding of the $^{125}$I-Cu-OxLDL to the macrophages efficiently (70-85%) in a dose dependent manner. The binding of $^{125}$I-Cu-OxLDL was not effected by the presence of the non-specific human IgG Fab, demonstrating that the inhibition was specific and that IK17 could effectively mask the epitope on the OxLDL that was seen by the scavenger receptors.

Macrophage OxLDL Degradation Assay

Macrophages were harvested and plated by the same method as in the binding assay above. Specific concentrations of $^{125}$I-Cu-OxLDL or $^{125}$I-MDA-LDL in serum free media was added to each well in the absence or presence of competitors for 5 hours at 37° C. The amount of lipoprotein degraded was determined by the amount of $^{125}$I-labeled trichloroacetic acid (TCA)-soluble (noniodide) material present in the medium. IK17 inhibited the degradation of $^{125}$I-Cu-OxLDL by macrophages by 50-65% in a concentration specific manner. The degradation of $^{125}$I-Cu-OxLDL and $^{125}$I-MDA-LDL were not effected by the presence of the non-specific human IgG Fab, demonstrating that the inhibition was specific and that IK17 could effectively mask the epitope on the OxLDL that was seen by the scavenger receptors.

In both the binding and degradation assays, the amount of lipoprotein bound or degraded was calculated as per mg of cell protein and the result expressed as % of control in the absence of any competitor.

Binding of IK17 to Apoptotic Cells and Inhibition of Macrophage Uptake.

FACScan: Dexamethasone treated apoptotic thymocytes were harvested and washed in ice cold PBS with 0.1% BSA. $1 \times 10^6$ cells were incubated with 50 µg/ml of IK17 or an isotype matched control human IgG(Fab) in PBS with 0.1% BSA at 4° C. for 20 minutes, washed and then incubated in for another 20 minutes with 10-20 µg/ml of propidium iodide (PI) and immediately analyzed by fluorescence activated cell sorting (FACS) analysis. PI staining allows for the separation of apoptotic and viable cells. The sorted cells were further analyzed for their ability to bind IK17. IK17 was found to bind apoptotic cells, but not viable cells indicating that cells undergoing apoptosis display epitopes recognized by IK17.

Phagocytosis assay: Phagocytosis of apoptotic thymocytes was determined as described by Chang et al., 1999. Macrophages were elicited and plated as described above. Cells were treated with dexamethasone and suspended in 0.5 ml of PBS with 0.1% BSA and labeled with Calcein AM$^R$ from Molecular Probes for 15 minutes at 37° C. Cells were washed and resuspended in supplemented DMEM. To assess phagocytosis, labeled apoptotic thymocytes were added to macrophage containing wells in the absence or presence of IK17 or non-human Fab as competitor, and incubated at 37° C. for 90 mm. Wells were washed. Macrophages were harvested and fixed. Fluorescence was analyzed by FACS. Cells were sorted by size to select for macrophages and not smaller cells. Fluorescent labeling of macrophages indicated the uptake of the labeled apoptotic cells. These studies revealed that the uptake of apoptotic cells was inhibited by 43% by IK17, indicating that IK17 is able to mask the epitope on apoptotic cells that is recognized by macrophage scavenger receptors.

Immunohistochemistry was performed on lesions of various stages from human and rabbit arteries. Sections from most of these tissues have been used previously in a number of studies and characterized in terms of the presence of macrophages and oxidation specific epitopes. Tissues were obtained during surgery or autopsy and fixed, sectioned, and stained by methods known to one skilled in the art. Staining of atherosclerotic lesions in human and rabbit arteries indicated that the epitopes recognized by IK17 occur mostly in the necrotic core. Macrophage-rich early lesions and shoulder areas of transitional lesions showed very little IK17 staining. Only a few human coronary lesions contained pockets of weak cellular staining. In contrast, strong IK17 staining was found in necrotic areas of advanced lesions of human coronary arteries and in the core of classical atheromas in human brain arteries. Similarly, in aortas from a rabbit model system of atherosclerosis, IK17 stained necrotic areas whereas only weak staining of early lesions and superficial macrophages was detected.

These results are in contrast to staining patterns obtained with antisera and Mabs against oxidation specific epitopes that had been induced by immunization with homologous oxidized LDL or with natural Mabs cloned from atherosclerotic apo E$^{-/-}$ mice. All of these antibodies consistently showed stronger macrophage-associated and diffuse extracellular staining in early lesions in humans, rabbits, and mice with relatively weaker staining in necrotic areas.

Optimization of IK17 For Use

The cDNA that codes for IK17 can be readily manipulated in a randomized or directed manner to optimize it for use in imaging and other applications. Coding sequences for linkers to attach labeling reagents, small molecules, or pharmaceuticals can be engineered into the cDNA. Additionally, IK17 itself can be modified to improve stability, increase plasma elimination rate to decrease background and increased tissue uptake rate. The coding sequence can be subjected to mutagenesis and screened against model compounds other than MDA-LDL to obtain antibodies that have slightly different specificities. Modifications can be made to optimize expression levels in the system of choice.

Conversion of IK17 Into scFv

After analyzing the cDNA sequence of IK17, PCR primers were designed to create a human scFv from the parental pComb3H vector that harbors the cDNA for VL and VH genes of IK17. To amplify the variable gene rearrangements, one VH (400 base pair) amplification and one Vk (350 bp) amplification was performed. The products of each reaction were separately pooled and ethanol precipitated. To perform an overlap PCR, aliquots of the Vk product were mixed with equal amounts of the VH product. The primers were created with identical sequences in the downstream portion of the Vk products and the upstream portion of the VH products to enable the creation of in-frame genes encoding scFv by overlap PCR. A 750 bp product for the Vk-linker-VH product was confirmed and was agarose gel size fractionated. The Vk-linker-VH sequence was then subcloned into Sfi site of prokaryotic expression vector pARA, which has an arabinose inducible promoter for high level expression and a polyhistidine tag for affinity purification using a nickel column. The sequence of scFv IK17 has been determined and consists of entire Vk region and entire VH region (125 amino acids each) connected by a seven amino acid linker having a molecular weight of approximately 30 kD. Immunology testing has shown that scFv IK17 has very similar binding properties as Fab IK17. In addition, scFv IK17 displays 50 to 500 greater binding activity to Cu-OxLDL and MDA-LDL than that of its parent Fab as assayed by chemiluminescent ELISA.

Labeling Technique for Noninvasive Imaging.

IK17 can be genetically or chemically engineered to contain $^{99m}$Tc binding sites for nuclear scintigraphy imaging. In vivo SPECT imaging can be carried out in a number of hosts atherosclerosis. Because nuclear scintigraphy may not have ideal resolution to detect small lesions, IK17 can be labeled with gadolinium or echogenic liposomes for magnetic resonance and transvascular or intravascular ultrasound imaging, respectively.

Conjugation of Human MAbs to Echogenic Liposomes for Transvascular Enhancement of Atherosclerotic Lesions.

Recently, antibody-conjugated echogenic liposomes have been developed for site-specific intravascular (30 MHz) and transvascular (15 MHz) image enhancement. Anti-fibrinogen and anti-intercellular adhesion molecule-1 (anti-ICAM-1) antibodies have been conjugated to acoustically reflective liposomes and images obtained in animal models of thrombi and atherosclerotic lesions. These acoustic liposomes consist of a 60:8:2:30 molar mixture of phosphatidylcholine: phosphatidyl-ethanolamine: phosphatidylglycerol:cholesterol and are prepared by a dehydration/rehydration mixture. They are multilamellar with well separated lipid bilayers and internal vesicles which confers echogenicity. Their mean size is ~800 nm as measured by quasielastic light scattering. These liposomes are stable in circulation, do not trap gas, pass through pulmonary capillaries and retain their properties at 37° C., even after conjugation with antibodies. The antibodies are thiolated with N-succinimidyl-3-(2-pyridyldithio) propionate, reduced, and conjugated with the liposomes by creating a thioether linkage between the antibody and phospholipid. The conjugated antibodies are stable and have a long shelf half-life. Atherosclerotic lesions are known to have increased permeability, which enhances penetration into the deeper areas of the plaque. Plaques with the thinnest "caps"—the endothelial/smooth muscle cell barrier overlying the atheroma—and the ones most vulnerable to rupture, are also the most permeable. Imaging is carried out as described below.

Gadolinium($Gd^{3+}$)-labeled scFv Antibodies

An alternative imaging method that provides enhanced resolution (<0.5 mm), magnetic resonance imaging (MRI), is evaluated by $Gd^{3+}$-labeling IK17 as a contrast agent. MRI has the advantages of rapid acquisition, increased resolution, absence of radioactivity and the ability to image the vessel wall without interference from signal in the vessel lumen. However, because free $Gd^{3+}$ as a contrast agent is toxic, it is used in clinical MRI imaging bound to diethylenetriaminepentaacetic acid (DTPA). Precedent exists for conjugating $Gd^{3+}$ to MAbs by reacting cyclic-diaminetriaminepentaacetic acid anhydride (c-DTPA) with the MAb. Initial attempts using this technique were suboptimal but subsequent studies have shown that polylysine-DTPA-$Gd^{3+}$-coupled antibodies can be used for tumour imaging with up to 30 Gd 3+ions conjugated without significantly affecting antigen affinity. Previous studies using $Gd^{3+}$-labeled MAbs have either directly bound $Gd^{3+}$ to available NH2 groups or chemically conjugated polylysine. The natural site for coupling DTPA is limited in scFv (single chain antibody) molecules. Therefore, we genetical fused several clusters of polylysine groups (6-30 in length) to the N-terminal or C-terminal of scFv MAb and react this with c-DTPA. Although other amino groups may potentially react, the availability of polylysine in the tail of the molecule should allow preferential site-directed labeling. The bioengineering of the polylysine site was done by PCR using primers encoding six lysine residues and restriction site for cloning at both 5' and 3' ends.

Imaging with $^{99m}$Tc-labeled MAb.

$^{99m}$Tc-labeling of oxidation specific antibodies has been previously described (Tsimikas et al., 1999). $^{99m}$Tc-IK17 intravenously injected into atherosclerotic and normal mice and rabbits and is analyzed for the pharmacokinetics, organ distribution and aortic plaque uptake. For in vivo imaging, 1-5 mCi are intravenously injected in hypercholesterolemia prone rabbits and imaging performed with a dual detector ADAC vertex model gamma camera set to a 20% window for $^{99m}$Tc (VXUR collimator) equipped with ADAC Pegasys™ computer software. In vivo images planar (anterior, posterior and 45° oblique positions) and SPECT will be acquired on a 256×256×12 matrix for a minimum of $1\times10^6$ counts at 10 minutes post injection. Repeat imaging is be performed for 3-500,000 counts at various timepoints based on the optimal target to background ratio derived from in vivo uptake data. Imaging studies using whole Mab often had a low signal to noise ratio due to the prolonged half-life of the $^{99m}$Tc-MAb in the circulation. Injections of the antigen, prior to imaging speed plasma clearance of the antibody, reducing the background for imaging. The use of Fab, scFv, or smaller fragments, can abrogate this problem under certain imaging conditions as the Fabs and scFvs have a very short half lifes (<30 minutes) and injection of antigen may not be required. When the signal to noise ratio is not favorable, injections of MDA-LDL, Cu-OxLDL, or other appropriate antigen is injected to clear the background signal.

Imaging with $Gd^{3+}$-labeled MAb.

Labeling of $Gd^{3+}$ to the antibody-DTPA complex has been previously described (Lister-James, et al, 1996; Wu et al, 1995). In vivo uptake assays are carried out with $^{153}Gd$-IK17 in mice and rabbits and the pharmacokinetics, biodistribution and aortic plaque uptake of IK17 is determined. In vivo imaging will then be performed in rabbits with a 1.5 T GE MRI scanner with a small surface coil Transvascular Enhancement of Atherosclerotic Lesions with Echogenic Liposomes Conjugated with MAb.

Native IK17 or IK17 modified by the addition of cysteines to the C- or N-terminus of the protein is thiolated and conjugated to liposomes. A 12 MHz imaging catheter (Acuson) is used for imaging (resolution<1 mm). Rabbits prescreened for evidence of lesion and are injected with 2-4 ml of MAb-conjugated liposomes, unconjugated liposomes and normal saline. Videodensitometric analysis of liposome brightness is then be carried out to assess uptake.

In vivo Plaque Uptake Assay to Determine Presence or Progression/Regression of Atherosclerotic Lesions To assess atherosclerotic lesions in vivo, labeled IK17 is injected into humans or animals having, or suspected of having, atherosclerotic disease. After a predetermined amount of time, dependent upon the stability of the labeling reagent, the type of imaging to be performed (local or whole body) and pharmacokinetic considerations, imaging is performed. To assess the efficacy of a treatment regimen, localized quantitative imaging is performed (e.g. with SPECT). To determine if disease is present anywhere in the body, full body imaging is performed. By the use of radioactive tracers on IK17, the progression or regression of plaques can be monitored quantitatively over the course of treatment with repeated imaging at desired intervals.

Intravascular Imaging of Lesions

Presently available methods of angiography could be combined with the use of labeled IK17 for enhanced imaging. The limitations of angiography were discussed above. Labeling of plaques before imaging would allow for the detection of smaller and more diffuse plaques that do not yet occlude the artery. IK17 labeled with $^{99m}Tc$, gamma radiation or echogenic liposomes could be detected intravascularly by the use of catheters. This would increase the prognostic value of the method by providing a means to determine the composition of the lesion.

In Vitro Assay for the Presence of Atherosclerosis

To determine if OxLDL forms recognized by IK17 are present in the serum of hosts suspected of having atherosclerotic disease, a sensitive, double-layered sandwich chemiluminescent immunoassays were developed. For example, an antiserum which binds to apo B, a component of LDL, was coated onto the bottom of a microtiter plate. A series of dilutions of plasma is added to allow binding of LDL, the middle of the sandwich. After extensive washing, an appropriate dilution of IK17 Fab is added as the top layer of the sandwich. The presence of IK17 Fab is detected using an alkaline phosphatase linked Fab specific anti-human antibody which is in turn detected by a colorimetric, luminescent or fluorescent assay. In a similar manner, an antiserum to human apoA1 can be used as the bottom layer to caputer HDL from plasma and allow the subsequent determination of IK17 epitopes in HDL. Finally, IK17 can be used as both top and bottom of the sandwich to obtain a measure of total IK17 epitopes.

Targeting of Atherosclerotic Drugs

One of the most challenging aspects of the development of pharmaceuticals is drug delivery. By the use of IK17, drugs for the treatment of atherosclerosis can be targeted to the required site of action, the atherosclerotic lesion. A panel of drugs are presently available for the treatment of atherosclerosis that work at the site of the lesion include thrombolytic agents, antioxidants, antimetalloproteinases, and immunomodulators. By targeting these drugs to their specific site of action, the active dose, and therefore the side effects, can be reduced. Additionally, active drugs with unfavorable pharmacokinetics can be linked to IK17 to improve their targeting to the plaque.

Development of Atherosclerotic Drugs

Immunization of $LDLR^{-/-}$ mice with OxLDL reduced the severity of the disease suggesting that antibodies of anti-OxLDL antibodies could be useful as therapeutic reagents. The Fab can be delivered directly or by means of a gene therapy vector as IK17 is expressed from a single gene.

A possible mechanism of action for the antibody is that by blocking the uptake of the OxLDL by macrophages, the formation of foam cells is inhibited and the progression of the disease is decreased. The binding site of IK17 for the OxLDL can be determined by direct structure determination or modeling, and used as a starting point for the development of small molecules to inhibit the uptake of OxLDL by macrophages.

Photodynamic Therapy

IK17 can be labeled with photodynamic compounds that emit energy upon stimulation with an appropriate wavelength of light that can be administered by the use of a catheterized light source. Activation of the compound may ablate the atherosclerotic plaque or inhibit the growth of the plaque.

REFERENCES

Barbas CFI, Lerner RA. Combinatorial immunoglobulin libraries on the surface of phage (phabs): Rapid selection of antigen-specific fates. *Methods*. 1991;2:119-12.

Chang, M.-K., Bergmark, C., Laurila, A., et al. Monoclonal antibodies against oxidized LDL bind to apoptotic cells and inhibit their phagocytosis by elicited macrophages: Evidence that oxidation specific epitops mediate macrophage recognition. *Proc. Natl. Acad. Sci. U.S.A.*, 1999;96:6353-6358.

Hörkkö, S., Miller, E., DudI, E., et al. Antiphospholipid antibodies are directed against epitopes of oxidized phospholipids: recognition of cardiolipin by monoclonal antibodies to epitopes of oxidized LDL. *J. Clin. Invest*. 1996;98:815-825.

Huse WD, Sastry L, Iverson SA, Klang AS, Alting-Mees M, Burton DR, Benkovic SJ, Lerner RA. Generation of a large combinatorial library of immunoglobulin repertoire in phage lambda. *Science*. 1989;246:1275-1281.

Lister-James J, Moyer BR, Dean T. Small peptides radiolabeled with 99 mTc. *Q J Nucl Med*. 1996;40:221-233.

Palinski, W., Hörkkö, S., Miller et al: Cloning of monoclonal autoantibodies to epitopes of oxidized lipoproteins from apo E-deficient mice. Demonstration of epitopes of oxidized LDL in human plasma. *J. Clin. Invest.* 1996;98:800-814.

Tsimikas S, Palinski W, Halpern SE, Yeung DW, Curtiss LK, Witztum JL. Radiolabeled MDA2, an oxidation-specific, Mab, identifies native atherosclerotic lesions in vivo. *J Nucl Cardiol* 1999;6:41-53.

Wu CC, Chang SW, Chen MS, Lee YT. Early change of vascular permeability in hypercholesterolemic rabbits. *Arterioscler Thromb Vasc Biol.* 1995;15:529-533.

Although an exemplary embodiment of the invention has been described above by way of example only, it will be understood by those skilled in the field that modifications may be made to the disclosed embodiment without departing from the scope of the invention, which is defined by the appended claims.

We claim:

1. An isolated human or humanized monoclonal antibody (Mab), fragment antibody (Fab) or single chain fragment (scFv) antibody having the binding specificity of the IK17 antibody;

wherein the human or humanized monoclonal antibody (Mab), fragment antibody (Fab) or single chain fragment (scFv) antibody comprises the variable light chain encoded by the nucleotide sequence of SEQ ID NO:1 and the variable heavy chain encoded by the nucleotide sequence of SEQ ID NO:2;

wherein the human or humanized monoclonal antibody, fragment antibody (Fab) or single chain fragment (scFv) is specific for oxidation specific epitopes found on copper-induced oidized low density lipoprotein (Cu—Ox-LDL) or malondialdehyde low density lipoportine (MDA-LDL);

wherein the human or humanized monoclonal antibody, fragment antibody (Fab) or single chain fragment (scFv) does not bind to native LDL;

wherein the human or humanized monoclonal antibody, fragment antibody (Fab) or single chain fragment (scFv) inhibits uptake of CuOxLDL by macrophages; and wherein the human or humanized monoclonal antibody, fragment antibody (Fab) or single chain fragment (scFv) binds the epitope in vivo at a detectably higher rate than the rate of binding to normal vasculature.

2. The isolated human or humanized monoclonal antibody (Mab), fragment antibody (Fab) or single chain fragment (scFv) antibody according to claim 1, wherein the antibody is a monoclonal antibody.

3. The isolated human or humanized monoclonal antibody (Mab), fragment antibody (Fab) or single chain fragment (scFv) antibody according to claim 1, wherein the antibody is a fragment antibody (Fab).

4. The isolated human or humanized monoclonal antibody (Mab), fragment antibody (Fab) or single chain fragment (scFv) antibody according to claim 1, wherein the antibody is a single chain fragment (scFv).

5. The isolated human or humanized monoclonal antibody (Mab), fragment antibody (Fab) or single chain fragment (scFv) antibody according to claim 1, wherein the antibody is human.

6. The isolated human or humanized monoclonal antibody (Mab), fragment antibody (Fab) or single chain fragment (scFv) antibody according to claim 1, wherein the antibody is humanized.

7. The isolated human or humanized monoclonal antibody (Mab), fragment antibody (Fab) or single chain fragment (scFv) antibody according to claim 1, wherein the antibody is detectably labeled.

8. The isolated human or humanized monoclonal antibody (Mab), fragment antibody (Fab) or single chain fragment (scFv) antibody according to claim 1 further comprising a therapeutic agent covalently linked to the antibody.

* * * * *

UNITED STATES PATENT AND TRADEMARK OFFICE
CERTIFICATE OF CORRECTION

| | | |
|---|---|---|
| PATENT NO. | : 7,575,873 B2 | Page 1 of 1 |
| APPLICATION NO. | : 10/706659 | |
| DATED | : August 18, 2009 | |
| INVENTOR(S) | : Joseph Witztum et al. | |

It is certified that error appears in the above-identified patent and that said Letters Patent is hereby corrected as shown below:

Please delete the paragraph at Column 1, lines 17-20 and replace with the following paragraph:

--This invention was made with government support under Grant Nos. HL-56989, HL-57505 and HL-07444 awarded by the National Institutes of Health. The government has certain rights in the invention.--

Signed and Sealed this

Eleventh Day of October, 2011

David J. Kappos
*Director of the United States Patent and Trademark Office*